(12) United States Patent
Severgnini et al.

(10) Patent No.: US 12,039,100 B2
(45) Date of Patent: *Jul. 16, 2024

(54) HYBRID INTERFACE FOR SIMULTANEOUS BIOSENSING AND USER INPUT

(71) Applicant: TOYOTA MOTOR ENGINEERING & MANUFACTURING NORTH AMERICA, INC., Plano, TX (US)

(72) Inventors: Frederico Marcolino Quintao Severgnini, Ann Arbor, MI (US); Ercan Mehmet Dede, Ann Arbor, MI (US); Paul D. Schmalenberg, Ann Arbor, MI (US)

(73) Assignee: TOYOTA MOTOR ENGINEERING & MANUFACTURING NORTH AMERICA, INC., Plano, TX (US)

(*) Notice: Subject to any disclaimer, the term of this patent is extended or adjusted under 35 U.S.C. 154(b) by 0 days.

This patent is subject to a terminal disclaimer.

(21) Appl. No.: 18/309,712

(22) Filed: Apr. 28, 2023

(65) Prior Publication Data

US 2023/0266825 A1   Aug. 24, 2023

Related U.S. Application Data

(63) Continuation of application No. 17/076,135, filed on Oct. 21, 2020, now Pat. No. 11,675,436.

(51) Int. Cl.
*A61B 5/0533* (2021.01)
*A61B 5/16* (2006.01)
(Continued)

(52) U.S. Cl.
CPC ............ *G06F 3/015* (2013.01); *A61B 5/0533* (2013.01); *A61B 5/165* (2013.01); *A61B 5/18* (2013.01); *B25J 13/084* (2013.01); *G06F 3/014* (2013.01); *G06F 3/016* (2013.01); *G06F 3/0446* (2019.05); *A61B 2562/0247* (2013.01); *A61B 2562/164* (2013.01); *G06F 2203/04105* (2013.01)

(58) Field of Classification Search
CPC .......... G06F 3/015; G06F 3/014; G06F 3/016; G06F 3/0446; G06F 2203/04105; G06F 3/011; G06F 2203/011; A61B 5/0533; A61B 5/165; A61B 5/18; A61B 2562/0247; A61B 2562/164; B25J 13/084
See application file for complete search history.

(56) References Cited

U.S. PATENT DOCUMENTS 11,550,385 B2 * 1/2023 Severgnini .............. A61B 5/00
2020/0164175 A1 * 5/2020 Kim ..................... A61B 5/6891

* cited by examiner

*Primary Examiner* — Temesghen Ghebretinsae
*Assistant Examiner* — K. Kiyabu
(74) *Attorney, Agent, or Firm* — SHEPPARD, MULLIN, RICHTER & HAMPTON LLP; Daniel N. Yannuzzi

(57) ABSTRACT

Dynamically adjustable EDA measurement device may include: a dynamically formable base comprising a soft robotics material, wherein the dynamically formable base comprises a formable surface configured to be dynamically formed in response to input signals; and an EDA sensing layer affixed to the formable surface of the dynamically formable base, the EDA sensing layer comprising a plurality of electrodes arranged on a flexible substrate and configured to be connected to a power supply; wherein, in response to input signals, the formable surface of the dynamically formable base and the EDA sensing layer affixed thereto are reformed into a desired contour.

20 Claims, 10 Drawing Sheets

(51) Int. Cl.
*A61B 5/18* (2006.01)
*B25J 13/08* (2006.01)
*G06F 3/01* (2006.01)
*G06F 3/044* (2006.01)

HYBRID INTERFACE FOR SIMULTANEOUS BIOSENSING AND USER INPUT

CROSS-REFERENCE TO RELATED APPLICATIONS

This application is a continuation of and claims the benefit of U.S. patent application Ser. No. 17/076,135 filed Oct. 21, 2020, which is hereby incorporated herein by reference in its entirety for all purposes.

TECHNICAL FIELD

The present disclosure relates generally to biosensing, and in particular, some implementations may relate to a conformable biosensor for various applications.

DESCRIPTION OF RELATED ART

User-facing technology in passenger vehicles has evolved dramatically over recent years, and some vehicles have taken advantage of the latest advancements available. Accordingly, contemporary user interfaces are being tasked to allow the user to control greater functionality than ever before as well as to access a greater amount of information. Although today's user interfaces in the cabin are far from the simple switchgear that was common in $20^{th}$ century vehicles, these interfaces are still limited to somewhat conventional applications of buttons, knobs and touchscreen interfaces.

In addition, vehicles are increasingly incorporating technology to sense and utilize bioinformatics from vehicle passengers. Bioinformatics information is used in a number of places, including vehicle safety systems to sense driver awareness and capacity. Some biosensing devices capable of measuring Electrodermal Activity (EDA) have been used to measure emotional state of the driver, which can be used to recognize driver stress levels. These methods typically require fixed electrodes adhered to the skin, such as those used with ECG devices. Accordingly, conventional biosensing devices for EDA measurements are not well suited to the passenger cabin.

BRIEF SUMMARY OF THE DISCLOSURE

Various embodiments of the disclosed technology relate to each hybrid surface for user input that allows a combination of touch input for actuation and sensing of Electrodermal Activity (EDA). Embodiments may be configured to include the capability to record EDA without requiring traditional fixed electrodes glued to the skin. In various embodiments, data collection may be realized (e.g., continuously) when the skin of the user (e.g., the Palm of the user's hands) contacts the device's surface. Embodiments may enable easy and seamless data collection without requiring electrodes affixed to the user's skin.

Embodiments may also utilize shape-changing materials, such as Liquid-Crystalline Elastomers (LCEs) to implement the touch input surfaces. Use of LCEs or soft robotics can allow configurable or conformable shapes to better suit desired applications. For example, hybrid surfaces can be conformed to accommodate the Palm of the operators hands. As another example, the hybrid surfaces can be configured to be adjusted to provide a tactile queue or feedback to the user.

In various embodiments, a dynamically formable electrodermal activity (EDA) sensor may include: a dynamically formable base comprising a soft robotics material, wherein the dynamically formable base comprises a formable surface configured to be dynamically formed in response to input signals; and an EDA sensing layer affixed to the formable surface of the dynamically formable base, the EDA sensing layer comprising a plurality of electrodes arranged on a flexible substrate and configured to be connected to a power supply; wherein, in response to input signals, the formable surface of the dynamically formable base and the EDA sensing layer affixed thereto are reformed into a desired contour.

Systems may further include an actuation layer comprising a plurality of touch-sensitive actuation points, the actuation layer disposed between the EDA sensing layer and the formable surface.

Embodiments may further include a plurality of pressure sensors distributed at determined locations beneath the EDA sensing layer to sense pressure of a user's body part at the determined locations, and may further include a processor to provide the input signals to the dynamically formable base in response to the pressure measured at the determined locations to adjust the formable surface of the dynamically formable base to conform to the user's body part.

In embodiments, dynamically formable base may include a plurality of separately actuatable elements arranged in a matrix, such that controlling the input signals to each of the separately actuatable elements determines a result in contour of the formal surface. In embodiments, dynamically formable base may include a nonlinear soft robotics material.

Embodiments may further include a sensing module configured to evaluate a connection strength between each electrode of the EDA layer and the user's skin at a given time and to identify electrodes from which EDA measurements are to be made based on the evaluation. The sensing module may be further configured to determine an EDA of the user based on EDA measurements from identified electrodes.

In embodiments, the EDA of the user is determined based on a combination of measurements from the identified electrodes.

The dynamically formable base may be configured to be reformed to conform to at least a portion of a user's hand.

The dynamically formable base may be configured to be reformed to provide a haptic response to a user of the EDA sensor.

In some embodiments, a hybrid electrodermal activity (EDA) sensor and user input device may include: a flexible EDA layer comprising a first flexible substrate and a plurality of electrodes disposed on the first flexible substrate in a determined pattern; and a flexible actuation layer comprising affixed to the flexible EDA layer, the flexible actuation layer comprising a first pattern of electrical contacts disposed on a second flexible substrate and a second pattern of electrical contacts disposed on a third flexible substrate wherein the second pattern overlaps the first pattern.

In embodiments, the first, second and third flexible substrates comprise transparent substrates, and wherein the electrodes disposed on the first flexible substrate and the electrical contacts first and second pattern of electrical contacts disposed on the second and third flexible substrates comprise transparent conductive materials.

The hybrid EDA sensor and user input device may further include a plurality of pressure sensors configured to detect an amount of pressure applied by a user to the flexible EDA layer.

The hybrid EDA sensor and user input device may further include a sensing module configured to evaluate a connection strength between each electrode of the flexible EDA layer and a user's skin at a given time and to identify electrodes from which EDA measurements are to be made based on the evaluation.

The hybrid EDA sensor and user input device of claim may be further configured to determine an EDA of the user based on EDA measurements from identified electrodes.

The hybrid EDA sensor and user input device may be configured to determine the EDA of the user based on a combination of measurements from the identified electrodes.

In some embodiments a system for processing information from a plurality of electrodermal activity (EDA) sensors to determine an EDA of a user may include: a processor; a non-transitory memory coupled to the processor and configured to store instructions, the instructions, which when executed cause the processor to perform the operations including: receiving information from a plurality of electrodes of an EDA sensor; determining which electrodes of the plurality of electrodes of the EDA sensor are providing valid EDA information; and combining EDA information from the determined plurality of electrodes that are providing valid EDA information to arrive at an EDA measurement for the user. Combining EDA information may include computing a weighted average of EDA measurements from the determined plurality of electrodes.

In some embodiments a method of processing information from a plurality of electrodermal activity (EDA) sensors to determine an EDA of a user may include: receiving information from a plurality of electrodes of an EDA sensor; determining which electrodes of the plurality of electrodes of the EDA sensor are providing valid EDA information; and combining EDA information from the determined plurality of electrodes that are providing valid EDA information to arrive at an EDA measurement for the user. Combining EDA information may include computing a weighted average of EDA measurements from the determined plurality of electrodes.

Other features and aspects of the disclosed technology will become apparent from the following detailed description, taken in conjunction with the accompanying drawings, which illustrate, by way of example, the features in accordance with embodiments of the disclosed technology. The summary is not intended to limit the scope of any inventions described herein, which are defined solely by the claims attached hereto.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

Figure 1:
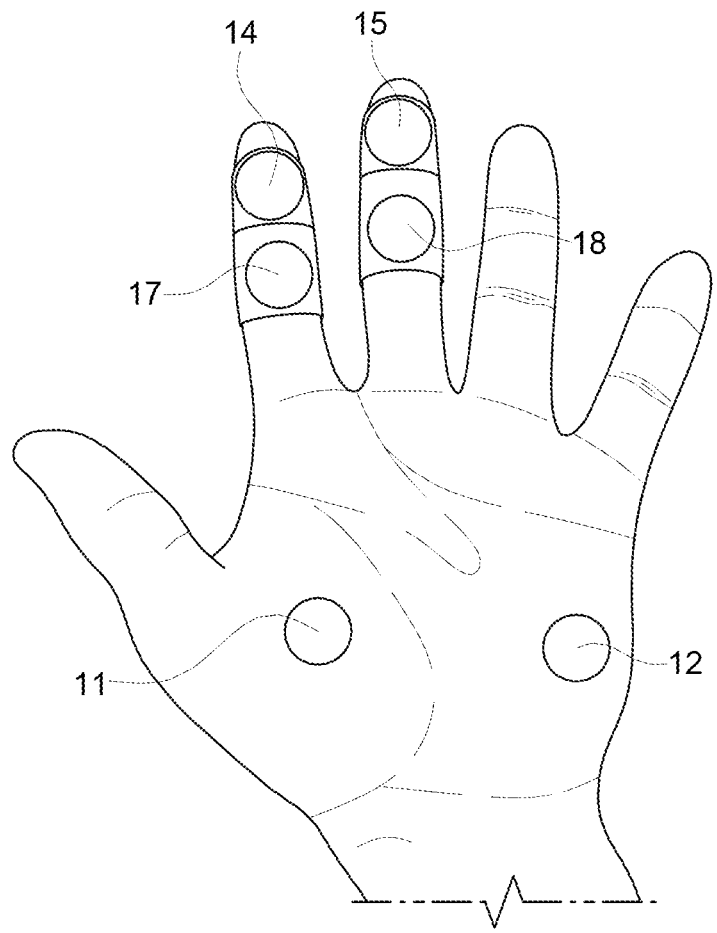
FIG. 1 illustrates an example of a typical EDA measurement setup using electrodes affixed to the skin.

The figures are not exhaustive and do not limit the present disclosure to the precise form disclosed.

DETAILED DESCRIPTION

Embodiments of the technology disclosed herein can provide a conformable hybrid surface configured to sense Electrodermal Activity (EDA) of a user and to be physically conformable to a desired shape. For example, the surface can be configured to be conformable to the users palm or hand. Various embodiments may be configured such that the surface can also act as a switch, touchpad or other actuator to provide a means for gathering user input as well as for sensing EDA. Embodiments may also be configured to allow the surface to be reshaped to provide tactile feedback to the user. For example, the shape can be configured to raise, become textured, to undulate or to otherwise be physically reshaped to provide information to the user tactilely.

Embodiments may be configured to include the capability to record EDA without requiring traditional fixed electrodes glued to the skin. In various embodiments, data collection may be realized (e.g., continuously or at determined times or intervals) when the skin of the user (e.g., the palm or finger(s) of the user's hand) is in contact with the device surface. Shape-changing materials, such as Liquid-Crystalline Elastomers (LCEs) or other soft robotics may be used to implement the touch input surfaces. Such implementations can allow configurable or conformable shapes to better suit desired applications. Different types of LCE (or like) structures may be combined in various embodiments to provide different types of haptic response, including surface deformations. Examples of materials other than LCEs may include other materials that may be implemented to generate changes in shape/volume/size, such as: pneumatic devices, liquid-pumping devices, shape-memory alloys, electric rubbers, and so on.

By varying the location and level of stimuli to one or more LCE structures, various shapes can be dynamically created in the deformable surface such that the user can differentiate through feeling different icons. Soft components that may be used for soft robotics include, for example, silicone elastomers, urethanes, hydrogels, hydraulic and other fluids. Embodiments may also use shape memory alloys and shape-memory polymers to provide desired deformations. Soft robotic components can be configured to have linear or nonlinear deformation characteristics to provide flexibility in accomplishing specific formations.

Embodiments may implement separate soft robotics components combined in a pixel-like arrangement to allow dynamic formation and reformation of particular shapes by controlling the adjustment of each 'pixel' or robotics element individually. Other embodiments may use soft robotics components with nonlinear deformation characteristics to provide the desired shapes.

EDA refers to variations of electrical properties of the skin as a result of factors such as the secretion of sweat. EDA might also be referred to as galvanic skin response, skin conductance, electrodermal response, among other terms. EDA measurements evaluate the electrical properties of the skin to measure sweat secretion. Particularly, EDA measurement techniques apply a low voltage to the skin to measure changes in skin conductance. Such techniques pass a current between two electrodes and measure and record the electrical resistance between these two electrodes. EDA is said to be an indicator of a level of arousal of the autonomic nervous system. Accordingly, EDA can be used to aid in determining whether a vehicle operator (or other individual) is undergoing increased levels of stress or experiencing other emotions such as, for example, fear and anger, and so on.

In some embodiments, EDA sensors may be layered on top of a shape changing (e.g., LCE) base to provide an EDA sensing structure that is also conformable or able to provide haptic feedback or other haptic response.

FIG. 1 illustrates an example of typical EDA measurements using electrodes affixed to the skin. Conventional solutions measure EDA by gluing a pair of electrodes to the skin at the Palm (e.g., at points 11, 12) or the fingers (e.g., at points 14, 15 or at points 17, 18). One reason electrodes are affixed to the skin such as by an adhesive is so that they make good electrical contact with the skin. Electrodes that are not firmly affixed to the skin may result in noise in the measurements or failure to achieve measurements at all.

Figure 2:
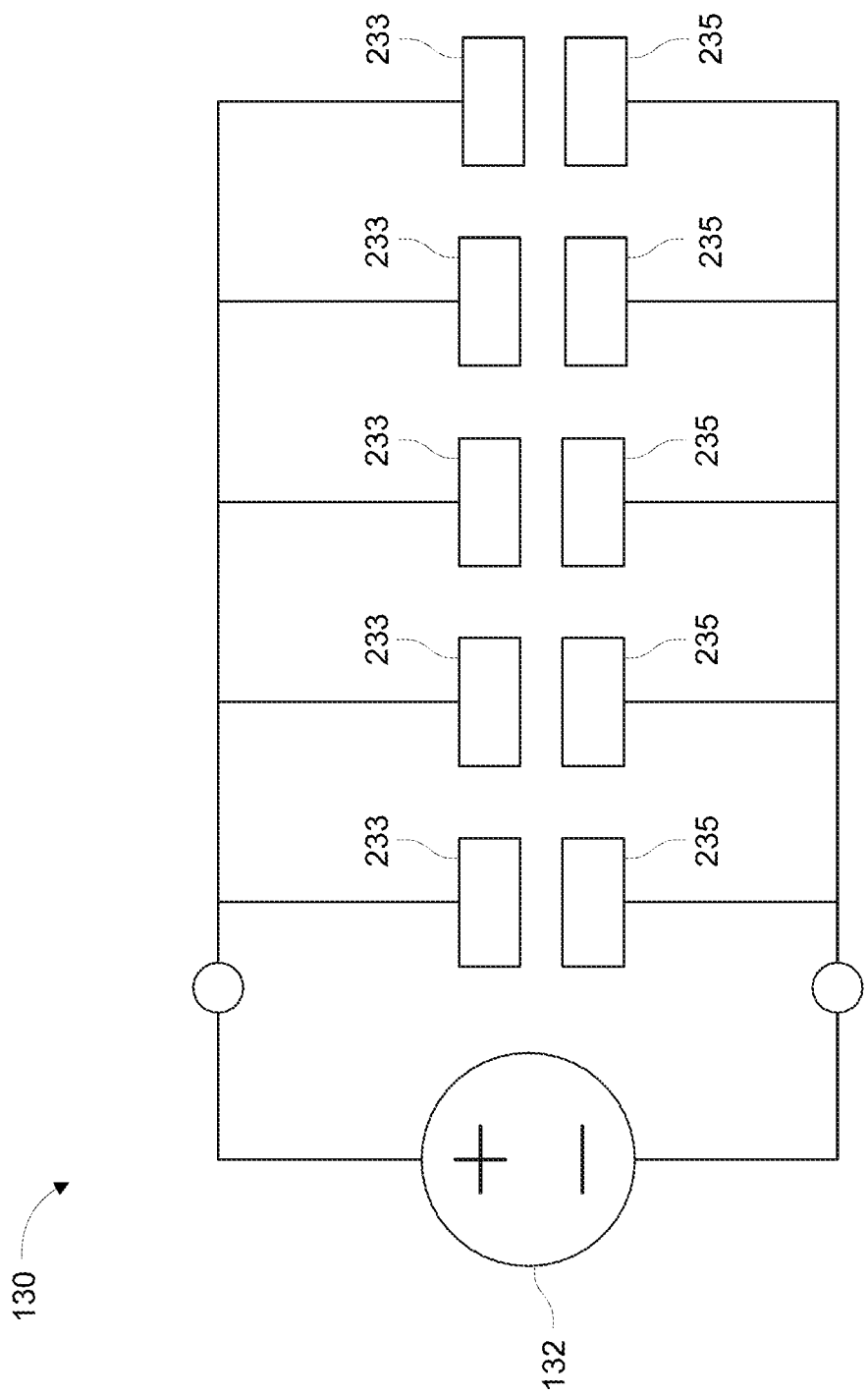
FIG. 2 illustrates an example surface that provides EDA sensing in accordance with various embodiments.

Embodiments may be configured to sense EDA without relying on electrodes affixed to the skin. Surfaces can be provided with a plurality of sensing locations that can make EDA measurements in response to the user contacting any of a number of different locations on a surface. FIG. 2 illustrates an example EDA surface that provides EDA sensing in accordance with various embodiments. This example illustrates an EDA sensing surface 130 that includes a plurality sensors made up of electrode-contact pairs 233, 235 that can be used to measure conductivity of the skin.

Although this example illustrates five sensors in a single row, embodiments may include different quantities of sensors in different patterns, in a single row, in multiple rows, in a staggered arrangement, or placed without regard to rows or like alignment considerations. The power supply 132 applies a voltage potential across each electrode-contact pairs 233, 235, which are arranged in the circuit in parallel. Electrodes can be manufactured using conductive materials such as, for example, copper, silver or silver chloride.

This example can be configured to measure changes in conductivity of the skin due to factors such as, for example, increases or decreases in the activity of sweat glands. Factors such as levels of agitation, attention, emotions, and other like conditions can affect the secretion of sweat by the eccrine glands. Changes in the amount of sweat changed the conductivity of the skin, which changes the resistance seen by each leg of the circuit. Based on Ohm's law, as resistance decreases the level of current increases, assuming a constant voltage. Accordingly, embodiments may be configured to measure current as a mechanism for measuring EDA.

Power supply 132 can be configured to supply a constant or time-varying voltage to the electrodes. Although not illustrated, the circuit may also include a small resistance (relative to the skin resistance) configured in series with the voltage supply in the electrodes. As noted above, the system can be configured to measure skin conductance by measuring the current flow through the electrodes. A current sensing circuit can be included for each leg of the circuit to measure the current at each leg. An example current sensing circuit detects the current and converts it to a measurable output voltage, which is generally proportional to the current through the path being measured. Any of a number of current sensing circuits can be used including, for example, a current sensing resistor in which the voltage drop across a resistor of a known resistance value can be used to derive a current according to Ohm's law, V=I*R. Other current sensing circuits can be used including, for example, operational amplifier circuits.

The EDA sensing surface 130 may be configured as a sheet or like structure into or onto which the electrodes are placed. The electrodes (e.g., electrode-contact pairs 233, 235) and associated interconnects can be printed or otherwise disposed on or partially encapsulated in a rigid or flexible material. Any of a number of different techniques may be used to provide conductive electrodes on top of the surface of the substrate such as, for example, screen printing, 3D printing, etching, deposition and other techniques. Because the interconnects (e.g. wires) don't require direct contact with the skin, they can be coated with insulating material or otherwise embedded within the substrate (e.g., below the outer surface) such that only the electrode-contact pairs 233, 235 are exposed to sense the users EDA data.

Figure 3:
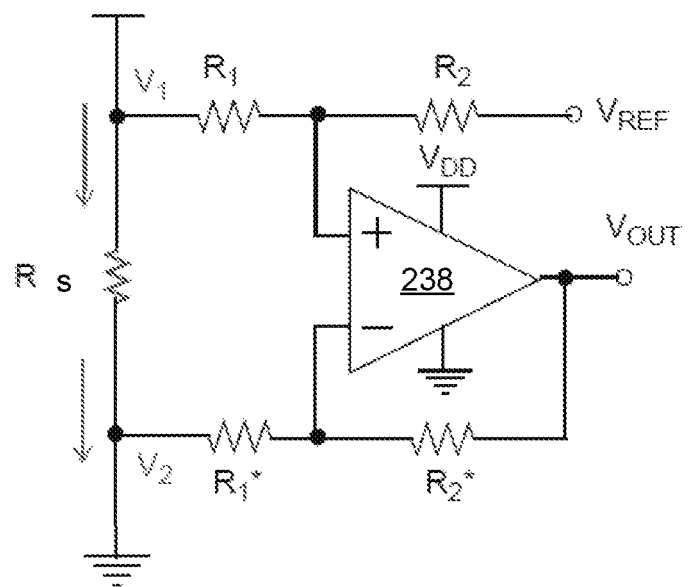
FIG. 3 illustrates an example current sensing circuit that may be used to sense current in each leg of a circuit in an EDA sensing surface in accordance with various embodiments.

FIG. 3 illustrates an example current sensing circuit that may be used to sense current in each leg of the circuit in EDA sensing surface 130 in accordance with various embodiments. This example circuit includes an operational amplifier 238 configured as a difference amplifier with four resistors R1, R2, R1*, R2*. In this example circuit, operational amplifier 238 amplifies the voltage drop across the sensing resistor Rs by the gain R2/R1. This can be useful in applications where the sensed voltage signal is small enough that it could benefit from amplification. The output voltage $V_{OUT}$ is proportional to the current. The output voltage $V_{OUT}$ is given by:

$$V_{OUT} = (V_1 - V_2) \cdot \left(\frac{R_2}{R_1}\right) + V_{REF}.$$

Embodiments may be configured to combine EDA sensing with user input interfaces in vehicles and in other applications. In most conventional applications, input interfaces, such as those used for head units, infotainment systems, climate control systems, and others are limited to providing a simple input option such as a button, switch or touchscreen. In some cases, haptic feedback may be provided to allow the user to determine based on touch whether the action was performed or not. For example, actuations of a touchscreen interface may be accompanied by a vibration or a tone to indicate that the input was accepted. Utilizing EDA sensing circuits, such as the example described with reference to FIG. 2, in combination with touch inputs (e.g., touch screens, touchpads etc.) embodiments can provide data collection that can be accomplished when the skin of the user's palm or fingers touches the input surface, or touches an accompanying surface near the input surface. Accordingly, embodiments may be configured to enable seamless data collection.

Embodiments may be implemented to form a hybrid sensing circuit that combines EDA sensing with a user input interface. For example embodiments may combine an EDA sensing layer (e.g., as in the example of FIG. 2) with a touch sensing layer (e.g., a touch sensing mesh as in the example of FIG. 4, below) to recognize user's touch. Accordingly, the electrode layer to sense EDA can be layered on top of an actuation layer configured to sense user input.

Figure 4:
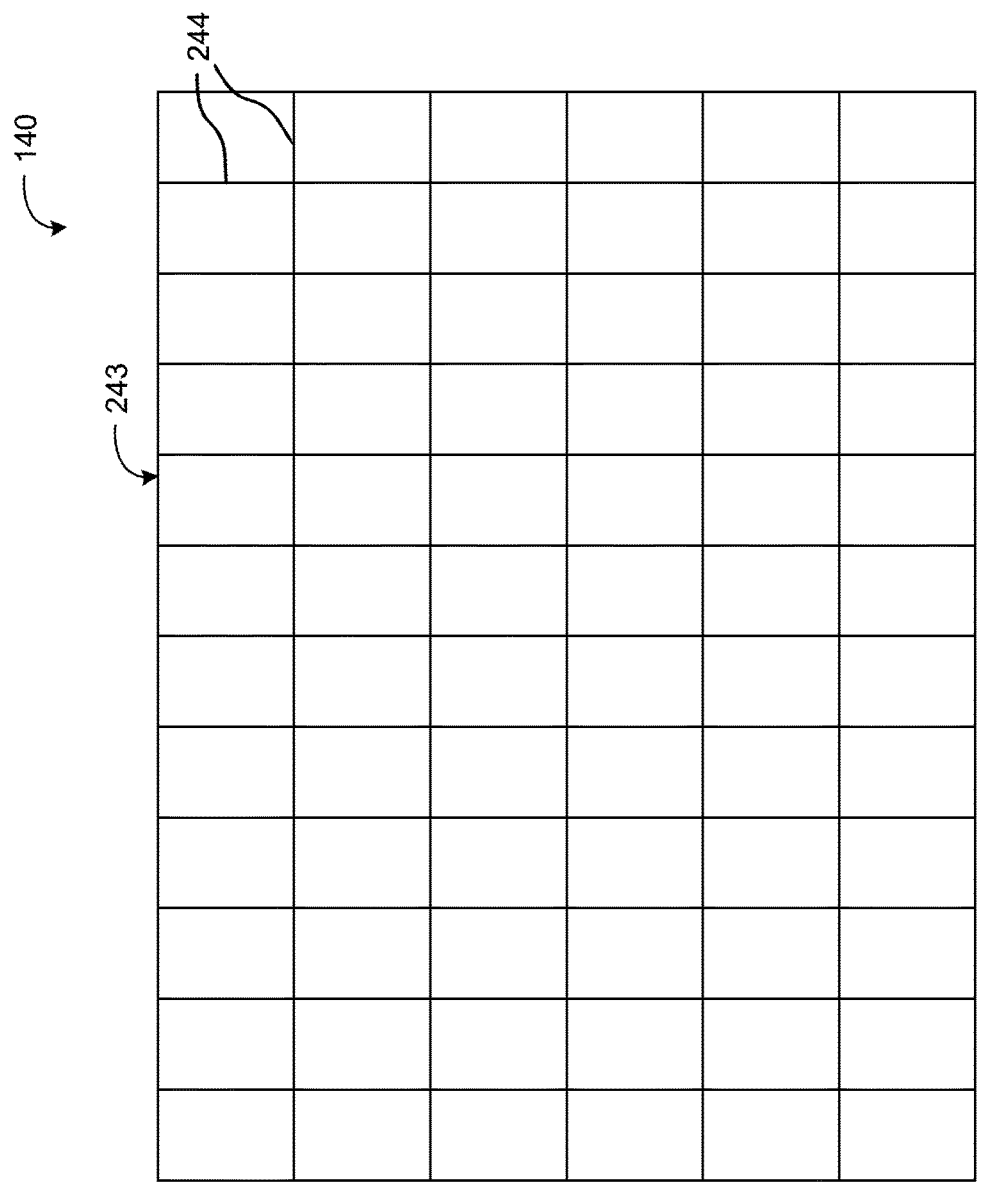
FIG. 4 illustrates an example actuation layer configured as a touch sensing mesh to sense a user's touch in accordance with various embodiments.

FIG. 4 illustrates an example actuation layer configured as a touch sensing mesh to sense a user's touch in accordance with various embodiments. In this example, actuation layer 140 includes a mesh of conductive lines 244 or patterns disposed on a flexible substrate 243. More particularly, actuation layer 140 may include two patterns of electrodes, each arranged on their respective substrates in an overlapping fashion. These can include a driving layer of electrodes and a sensing layer of electrodes separated by an insulator such that the electrodes can be used to detect the occurrence and location of a user's touch. In the example illustrated in FIG. 4, the two patterns of electrodes 244 are arranged as vertical and horizontal lines that cross one another at regular intervals. The capacitance value can be measured at each wire intersection, creating a capacitance matrix. A detection module can be included to monitor changes in capacitance values in this matrix to determine whether the user is touching the surface or not, and which part of the surface the user is touching. Additionally, embodiments may include a mesh of pressure sensors (not illustrated) to measure the amount of force with which the user's touch is being applied to the mesh.

Flexible materials may be used to implement either or both the EDA sensing layer and the actuation layer. This can allow flexibility when placing an EDA sensor or hybrid interface at various locations within the automobile or other vehicle or application. For example, where soft robotics or other like technology is utilized to allow the EDA sensor or the hybrid interface to be dynamically conformable to a desired shape flexible materials may facilitate this conformability. Flexible materials may include, for example, Mylar or the like, textiles, leathers or polymers. Examples of polymers may include polyethylene naphthalate (PEN), polyethylene terephthalateble (PET), polyimide (PI) and others. Embodiments may also use stretchable elastomers such as, for example, polydimethylsiloxane (PDMS). As noted above, the electrodes can be arranged in a desired pattern into disposed on the substrate in a manner such that they can come into contact with the user's skin.

The electrode layer is not limited in quantity of electrodes, arrangement electrodes, shape of the layer or other properties by the example illustrated in FIG. 2. Either or both the electrode layer and the actuation layer can be provided in the appropriate shape and size to accommodate the given application. The number and arrangement of electrodes in the EDA sensing layer can be likewise suited to the particular application. The number and shape of the electrodes can vary depending on the size of the surface and its location in the vehicle or other application.

Embodiments may be configured to utilize transparent conductive materials for the EDA sensing layer so that the structure implemented can be invisible to the naked eye. This can allow configurations in which the structure can be embedded in common cockpit surfaces such as leathers and vinyls. Transparent conductors may include, for example, transparent conductive oxides (e.g., indium tin oxide), glassy polymers or other transparent conductive materials.

Similar to the EDA layer, actuation layer 140 can be manufactured using flexible substrates to allow the actuation layer to be dynamically conformable. Also similar to the EDA layer, actuation layer 140 can be manufactured using transparent conductive materials to provide an invisible structure, which may be beneficial in aiding in the aesthetics of the installation.

A sensing module can be included to determine EDA based on current measurements and to determine touch inputs by the actuation layer. An example processing circuit utilized to implement a sensing module is illustrated and described below with reference to FIG. 10. Such a sensing module can include a processor or other circuitry used to determine current levels (e.g., based on a voltage level) at each electrode. The sensing module may also be configured to evaluate which electrodes have a better connection to the user's skin at a given time and use measurements from those one or more electrodes to measure EDA.

Embodiments may be implemented in which information from electrodes identified as providing a valid signal is used to measure EDA, and information from other electrodes is ignored or discarded. Embodiments may further be implemented in which information from the identified valid electrodes is combined to arrive at a EDA measurement. For example, the information from the valid electrodes can be combined as an average of EDA measurements from the electrodes, a weighted average (e.g., for example, based on determined quality of information from the electrodes) or other combination of information from the determined valid electrodes.

This can be accomplished, for example, based on pressure sensing at the EDA sensing layer or at the actuation layer. For example, pressure sensors may be included with the EDA sensing layer or the hybrid interface to measure pressure had some or all of the electrodes.

Evaluating which electrodes have a better connection to the user's skin at a given time might also be accomplished, for example, based on continuity of a signal from the EDA sensing layer or actuation layer. For instance, a signal that exhibits rapid variations may indicate the user is only making intermittent contact at that electrode.

Flexible substrates and flexible conductive materials (e.g., silver paste, copper paste, conductive films) can be used to allow the entire structure to operate as a flexible and conformable device. This can be utilized to allow the structure to be dynamically conformed using, for example, soft robotics. This can also allow the device to be implemented to conform to multiple different locations inside of the vehicle.

Figure 5:
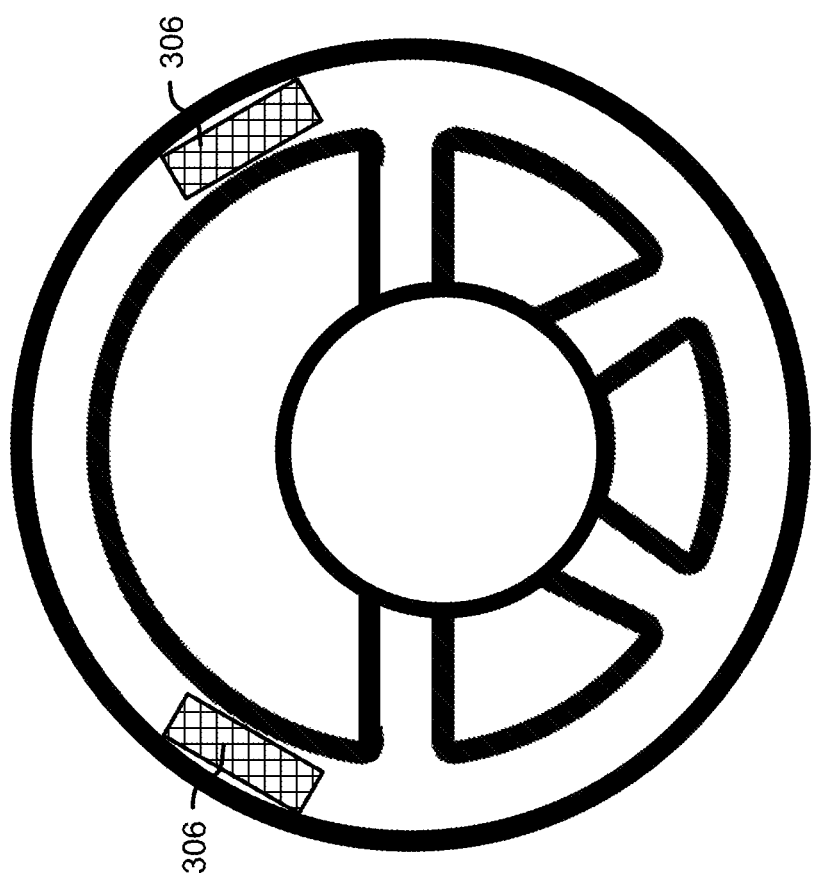
FIG. 5 illustrates an example embodiment in which EDA sensing surfaces are located on a vehicle steering wheel.

FIG. 5 illustrates an example embodiment in which EDA sensing surfaces are located on a vehicle steering wheel. In this example, EDA sensing surfaces 306 are located at the 10 o'clock and 2 o'clock and positions of the vehicle steering wheel. The EDA sensing surfaces can be configured as a flexible sensing surface to conform to the shape of the steering wheel. In some embodiments, the EDA sensing surfaces 306 can be configured as an aftermarket installation they can be wrapped around the steering wheel. In other applications, the EDA sensing surfaces 306 can be provided as factory equipment integrated into the steering wheel cover. As noted above, transparent conductors can be used to provide a device that is difficult to detect with the naked eye, thereby not interfering with the aesthetic nature of the vehicle. Although EDA sensing surfaces 306 are shown as two patches at the 10 o'clock and 2 o'clock positions of the steering wheel, they can be provided at other locations in addition to or instead of the 10 o'clock and 2 o'clock positions, but may be preferably positioned at locations commonly gripped by vehicle operators to improve the likelihood that measurements can be made. Also, the EDA sensing surfaces 306 can be smaller or larger than those shown in the example of FIG. 5, and can also be of a different shape.

Figure 6:
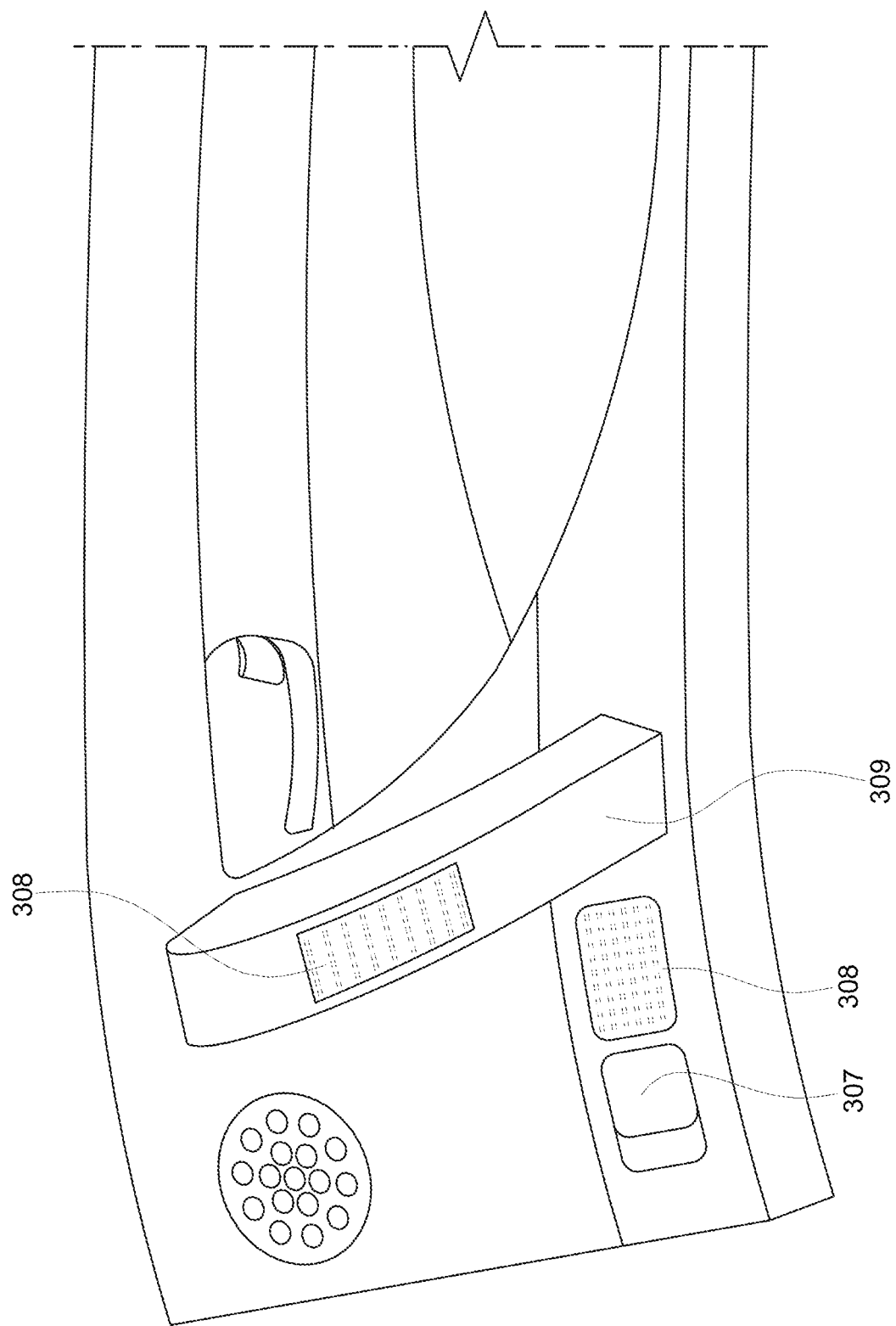
FIG. 6 illustrates an example embodiment in which EDA sensing surfaces are located at multiple locations inside a vehicle cockpit.

FIG. 6 illustrates an example embodiment in which EDA sensing surfaces are located at multiple locations inside a vehicle cockpit. In this example, EDA sensing surfaces 308 are located on the door handle 309 and adjacent to window switch 307. This illustrates examples that might be common or frequent touch points of a vehicle operator or passenger. As with EDA sensing surfaces 306, EDA sensing surfaces 308 may be configured in different shapes or sizes depending on where they are applied. They can also be fabricated using transparent materials to aid in their aesthetics.

Figure 7:
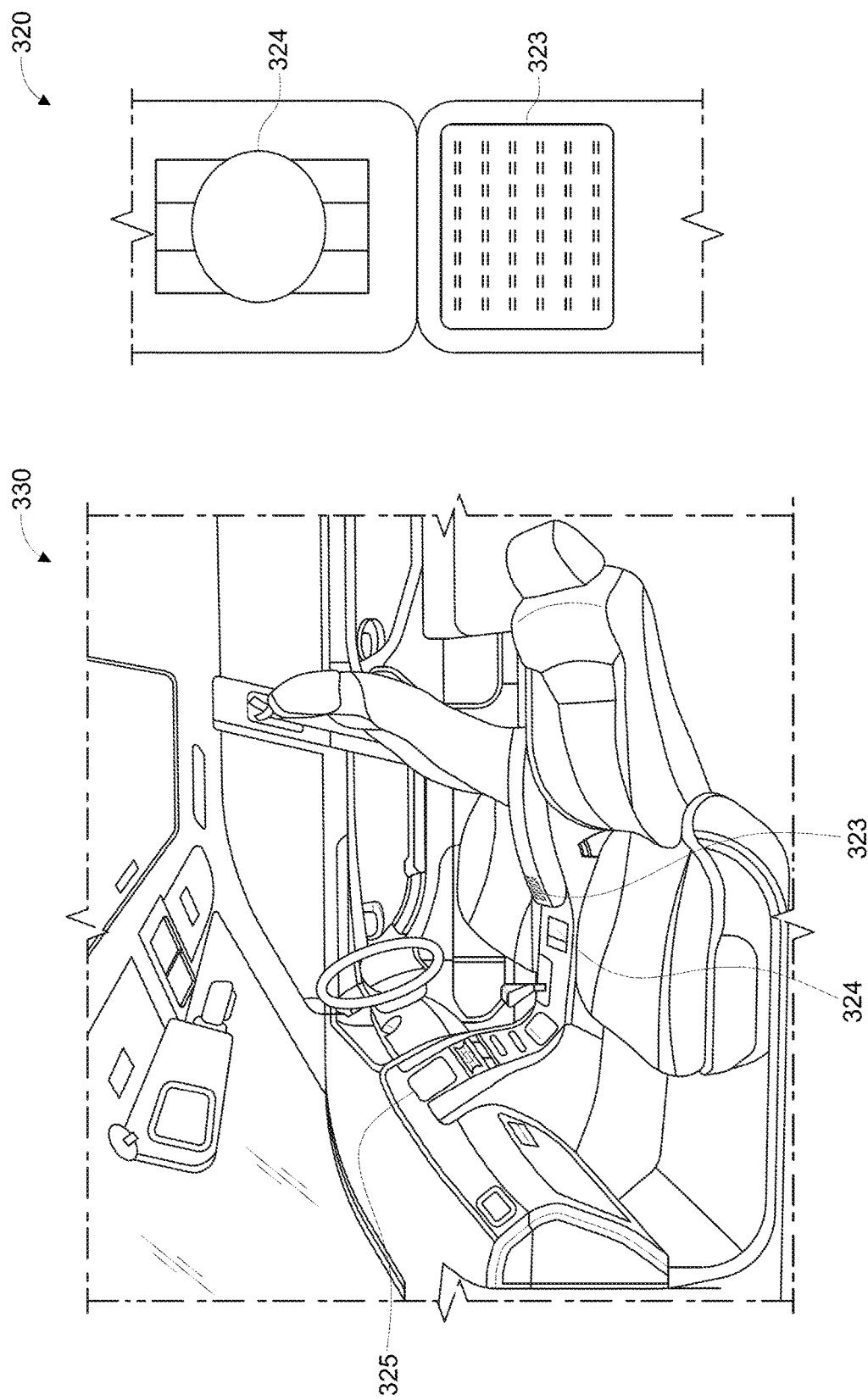
FIG. 7 illustrates an example embodiment in which an EDA sensing surface is located on the vehicle center console adjacent a touchpad or scroll wheel.

FIG. 7 illustrates an example embodiment in which an EDA sensing surface is located on the vehicle center console adjacent a touchpad or scroll wheel. View 330 illustrates a cockpit view of an EDA sensing surface 323 adjacent to a user interface 324 and also illustrates a head unit display 325. View 320 illustrates a top-down view of the vehicle center console with EDA sensing surface 323 adjacent user interface 324. In this example, EDA sensing surface 323 is located on the vehicle center console in approximately location where the vehicle operator's or passenger's palm may rest when operating user input 324. Accordingly, user EDA measurements may be made when the user is resting there palm on the arm rest at the location of EDA sensing surface 323.

An EDA sensing surface may also be positioned on the surface of touchpad or input wheel of user input 324 to sense a user's EDA when the user is touching the surface of user input 324. In EDA sensing surface may further be positioned on touchscreen interface 325. In these examples, a hybrid sensing surface may be used to provide a combination of EDA sensing and touch inputs sensing and user input 324 and touchscreen interface 325. This can allow either or both of these devices to be operated in a manner to gather EDA information while also sensing user input.

As noted above, embodiments may be implemented in conjunction with soft robotics or other shape changing services to allow the EDA device (whether or not implemented as a hybrid device with a user actuation layer) to be implemented in a manner such that the surface can undergo adjustments. Such adjustments might be made to conform to the shape of the user's hand, to provide a haptic response, or to otherwise change the shape or surface texture. The ability to conform to the shape of user's hand can increase the comfort for the user and make it easier and more likely that the user will rest their hands on the surface. This may in turn enable longer and more stable EDA readings.

Accordingly, embodiments of the present disclosure may provide a liquid crystal elastomer-based foundational device configured to provide the noted conformance to the user's hand or a haptic feel that may enable feedback regarding an actuator selection process or feedback to help identify a portion of the surface this should be pressed to provide a desired user input.

A formable surface may include an elastomer actuation region that may be made up of a plurality of liquid crystal elastomer (LCE) structures. Different types of LCE structures may be combined in various embodiments to provide different types of haptic feedback or desired surface deformations. Control systems may be implemented to control the location and level of stimuli applied to one or more LCE structures, to create various shapes dynamically in the deformable surface. In alternative embodiments, shape-memory alloys, E-rubbers and other shape changing materials may be used as well. These materials can be configured to change shape and volume when stimulated with the appropriate input such as light, electrical signals, or temperature. As noted, this can allow an EDA device, user input device, or hybrid EDA/input device to be dynamically formable such as to be conformable to the user's hand or to provide desired haptic feedback.

Haptic feedback may include more than just feedback regarding actuation (e.g. confirmatory vibration, etc.) but may also or alternatively include conforming the shape of the surface so that the user can differentiate different inputs based on their unique, reformed shapes. For example, a normally flat surface can be adjusted dynamically to provide a plurality of raised regions on the surface indicating actuation points (e.g., buttons) that can be pressed to provide user input. Embodiments may be implemented to create different button patterns for different circumstances. For example, button patterns can be created differently based on, for example, the vehicle system that the interface is currently controlling. Accordingly, there might be a different arrangement of buttons to control a climate control system than the arrangement to control an audio system. As another example, different button patterns can be generated based on user preferences. User profiles can be obtained and stored and user-specific button configurations generated dynamically for the identified then-current user.

As another example, button patterns may be dynamically created based on then-current circumstances. For example, the vehicle may detect a potentially dangerous situation and offer the operator the option of enabling a safety system (e.g., an ADAS system) in response to the dangerous situation. In this case, the vehicle can ask the operator (e.g., via synthesized voice) if he or she wants to enable the system and may instruct the operator to press the raised button of the touchpad in response.

Figure 8:
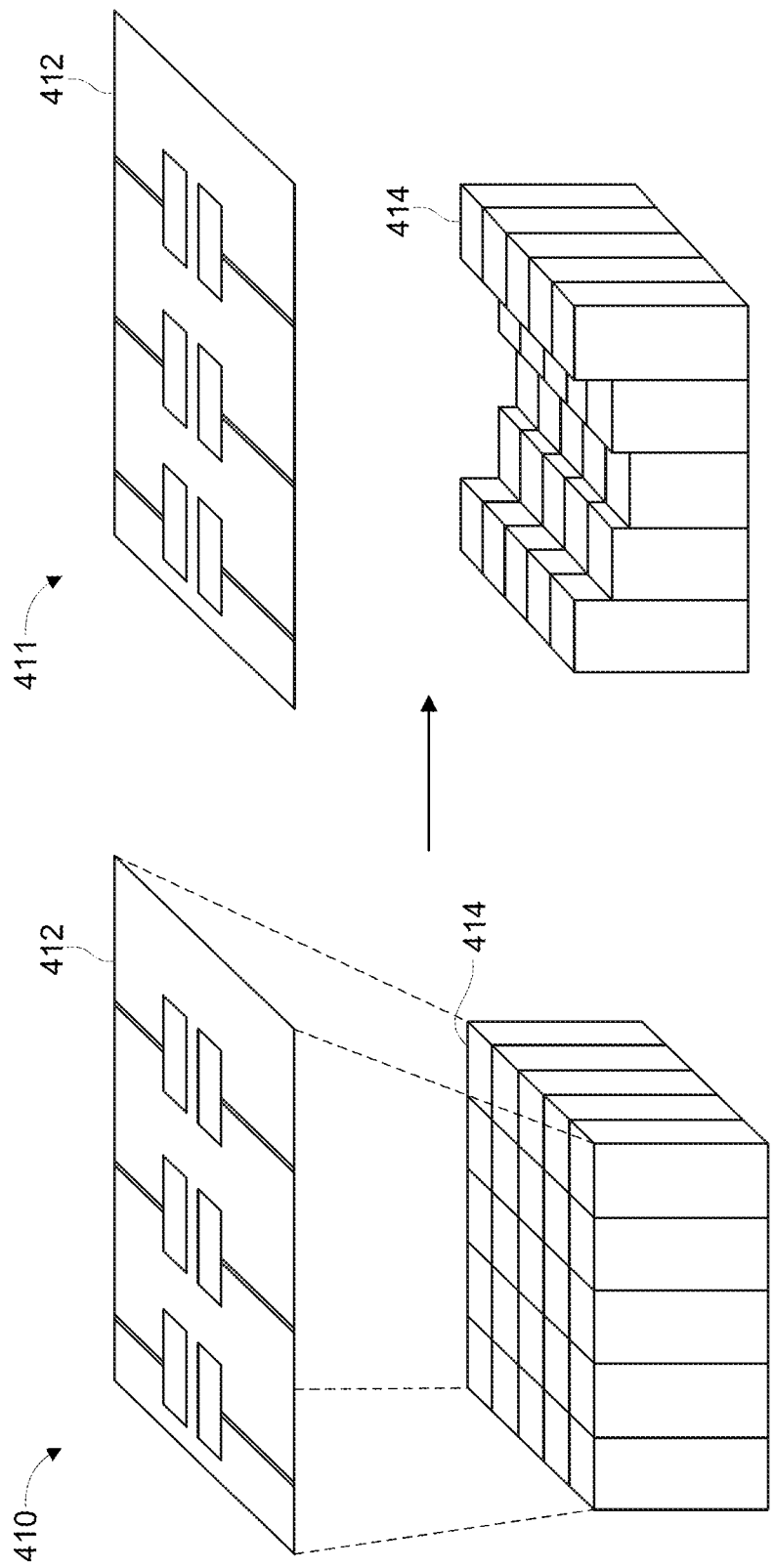
FIG. 8 illustrates an example of a structure for dynamically configurable EDA surface in accordance with various embodiments.

FIG. 8 illustrates an example of a structure for dynamically configurable EDA surface in accordance with various embodiments. In this example, an EDA layer 412 (e.g., EDA sensing surface 130) comprising a matrix of EDA electrodes can be positioned on a soft robotics-based matrix 414. Although not illustrated, an actuation layer (e.g., actuation layer 140) may also be included. These two layers can be affixed to soft robotics matrix 414, such that they conform to the surface of soft robotics matrix 414 when soft robotics matrix 414 is reconfigured.

Figure 9:
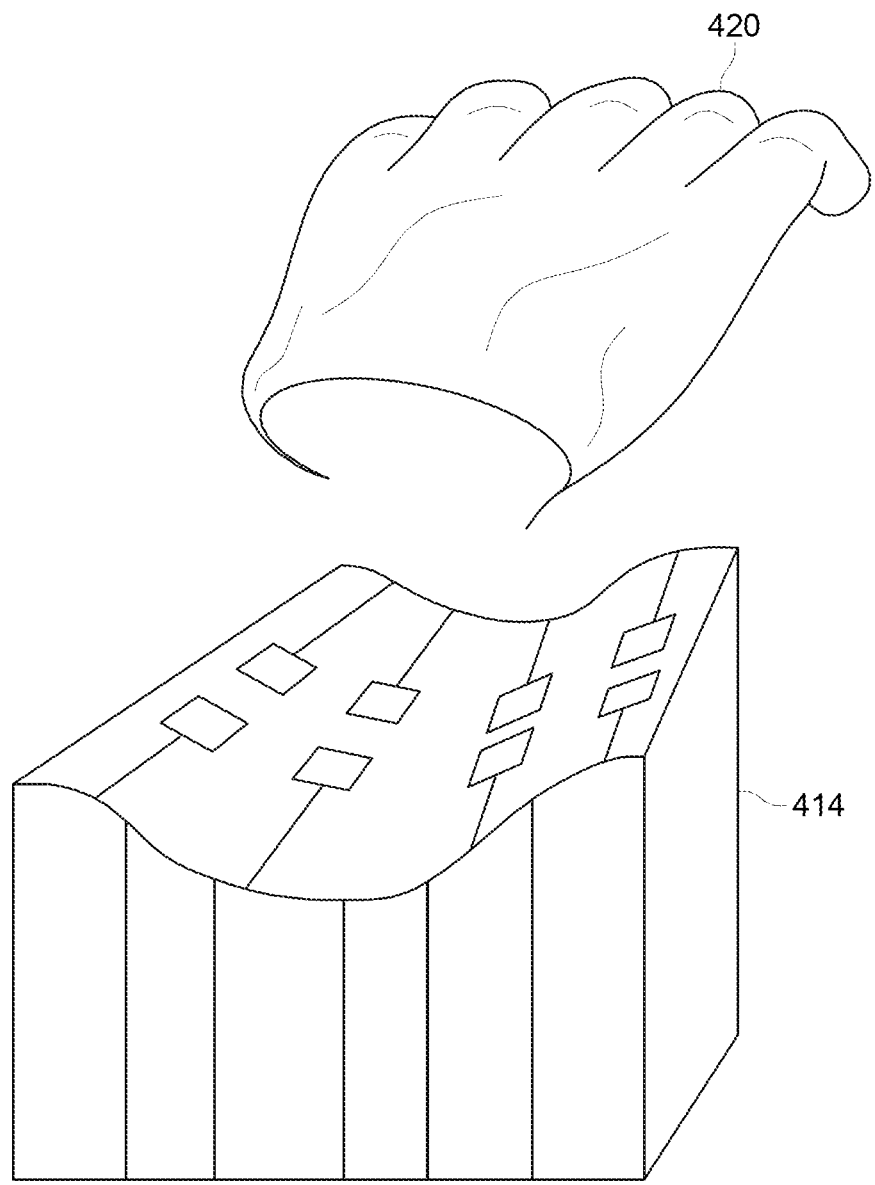
FIG. 9 illustrates an example in which soft robotics-based matrix 414 is re-shaped to conform to the user's hand 420, and further illustrates that the EDA layer 412 (and the actuation layer, if included) conform to the reshaped soft robotics-based matrix 414.

The touch sensing matrix on the actuation layer can be configured to detect the shape of the user's hand and this information can be used to actuate the tactile pixels in soft robotics-based matrix 414 accordingly. By doing so, the structure, including EDA layer 412 can accommodate the users hands more comfortably. Accordingly, EDA layer 412 and any included actuation layer can be composed of flexible, formable materials so that they can adequately adapt to the desired shape. In the example of FIG. 8, 410 illustrates soft robotics-based matrix 414 in a non-deformed configuration with a flat top surface. At 411, FIG. 8 illustrates soft robotics-based matrix 414 deformed by reducing the height of the interior rows of the matrix. FIG. 9 illustrates an example in which soft robotics-based matrix 414 is re-shaped to conform to the user's hand 420, and further illustrates that the EDA layer 412 (and the actuation layer, if included) conform to the reshaped soft robotics-based matrix 414.

While the examples of FIGS. 8 and 9 illustrate shape formation on a column-by-column basis, shape formation can also be controlled row-by-row or at a pixel level to create a variety of different shapes. The pixel size and quantity of pixels (i.e., resolution) can be adjusted based on the application to provide desired control over possible shapes and sizes of the shapes that can be created.

As illustrated above with reference to FIG. 7, one of the possible applications of embodiments disclosed herein is in a hand rest near a console-located user interface. However, given the flexible and compliant nature of various embodiments, the device can be easily incorporated into other regions of the vehicle or it can be used in applications other than in vehicles. For example, if a conformable structure is placed in the steering wheel, the tactile pixels could actuate to generate a grasp that feels more comfortable to each driver. Additionally, the touch sensing manage that forms the actuation layer could be used to allow the driver to execute commands without taking hands off the steering wheel. Actuation might be sensed, for example, by the user simply tightening the grip of one or more fingers on the steering wheel. As another example, the system can be configured to allow the user to use taps or swipe gestures to control various vehicle systems.

The EDA detection can be used to control a variety of vehicle system such as, for example, driver alerts (e.g., "you are getting sleepy and should consider taking a rest" or "you appear to be distracted and should focus on driving"), safety systems or other vehicle systems. The EDA detection system may also be used to provide a more sophisticated interface between the user's emotional state and the vehicles user interface. If for example, the system detects that the driver is distracted, the vehicle cockpit can be reconfigured to hide certain button options, thereby reducing or minimizing the opportunities to create further distraction. Likewise, if the driver is not distracted and road conditions are known to be safe, the system can enable more buttons allowing safe usage of peripheral functions.

The systems and methods disclosed herein are described in various examples as being implemented with passenger, cargo or other vehicles. However, the systems and methods disclosed herein are not limited to applications in vehicles and may be implemented in a number of other settings where it may be useful or desirable to monitor EDA.

Figure 10:
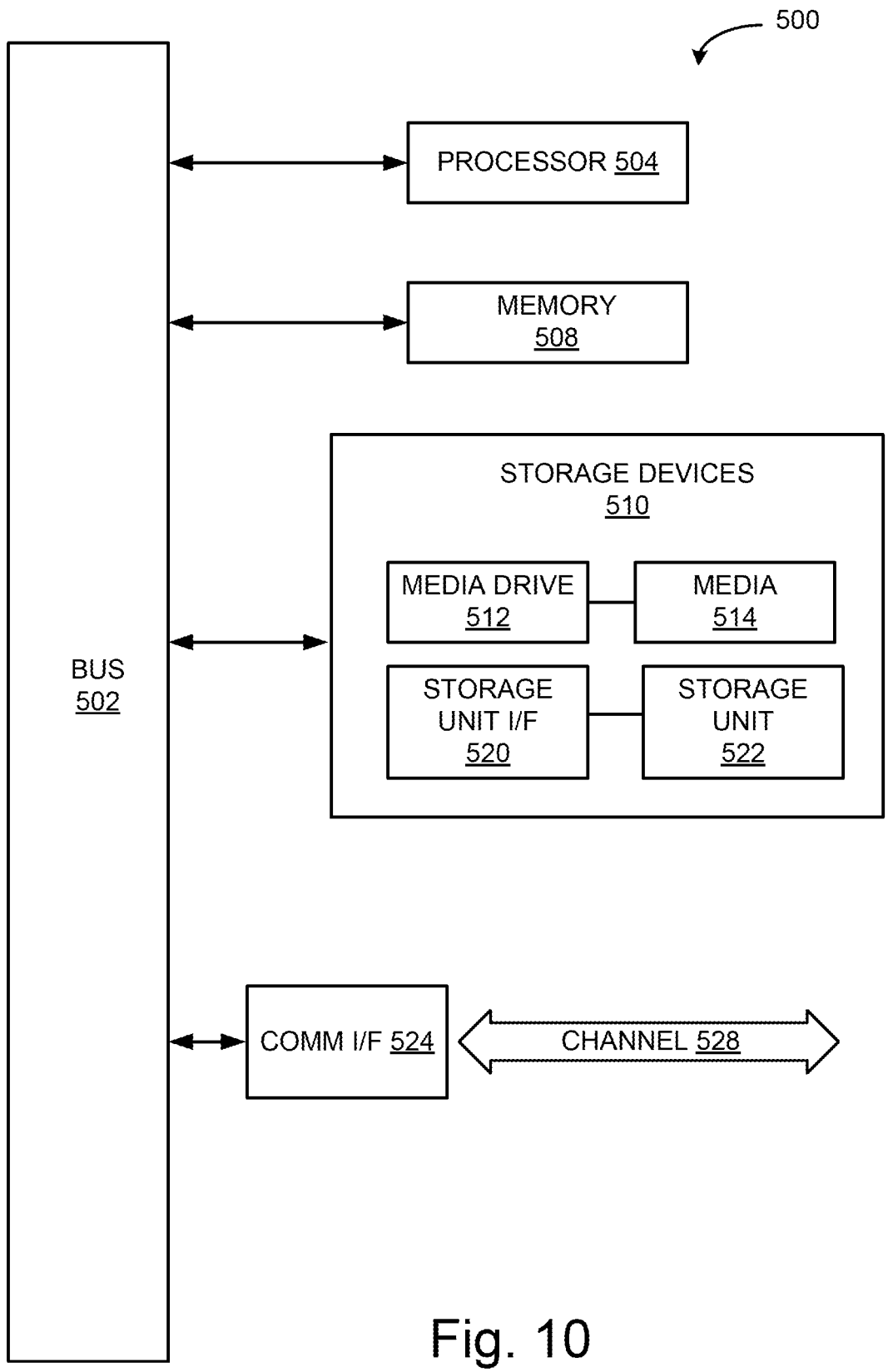
FIG. 10 is an example computing component that may be used to implement various features of embodiments described in the present disclosure.

As used herein, the term module may be used describe a given unit of functionality that can be performed in accordance with one or more embodiments of the present application. As used herein, a module might be implemented utilizing any form of hardware, software, or a combination thereof. For example, one or more processors, controllers, ASICs, PLAs, PALs, CPLDs, FPGAs, logical components, software routines or other mechanisms might be implemented to make up a module. Various components described herein may be implemented as discrete module or described functions and features can be shared in part or in total among one or more modules. In other words, as would be apparent to one of ordinary skill in the art after reading this description, the various features and functionality described herein may be implemented in any given application. They can be implemented in one or more separate or shared modules in various combinations and permutations. Although various features or functional elements may be individually described or claimed as separate components, it should be understood that these features/functionality can be shared among one or more common software and hardware elements. Such a description shall not require or imply that separate hardware or software components are used to implement such features or functionality.

Where modules are implemented in whole or in part using software, these software elements can be implemented to operate with a computing or processing component capable of carrying out the functionality described with respect thereto. One such example computing component is shown in FIG. 10. Various embodiments are described in terms of this example-computing component 500. After reading this description, it will become apparent to a person skilled in the relevant art how to implement the application using other computing components or architectures.

Referring now to FIG. 10, computing component 500 may represent, for example, computing or processing capabilities found within a self-adjusting display, desktop, laptop, notebook, and tablet computers. They may be found in hand-held computing devices (tablets, PDA's, smart phones, cell phones, palmtops, etc.). They may be found in workstations or other devices with displays, servers, or any other type of special-purpose or general-purpose computing devices as may be desirable or appropriate for a given application or environment. Computing component 500 might also represent computing capabilities embedded within or otherwise available to a given device. For example, a computing component might be found in other electronic devices such as, for example, portable computing devices, and other electronic devices that might include some form of processing capability.

Computing component 500 might include, for example, one or more processors, controllers, control components, or other processing devices. Processor 504 might be implemented using a general-purpose or special-purpose processing engine such as, for example, a microprocessor, controller, or other control logic. Processor 504 may be connected to a bus 502. However, any communication medium can be used to facilitate interaction with other components of computing component 500 or to communicate externally.

Computing component 500 might also include one or more memory components, simply referred to herein as main memory 508. For example, random access memory (RAM) or other dynamic memory, might be used for storing information and instructions to be executed by processor 504. Main memory 508 might also be used for storing temporary variables or other intermediate information during execution of instructions to be executed by processor 504. Computing component 500 might likewise include a read only memory ("ROM") or other static storage device coupled to bus 502 for storing static information and instructions for processor 504.

The computing component 500 might also include one or more various forms of information storage mechanism 510, which might include, for example, a media drive 512 and a storage unit interface 520. The media drive 512 might include a drive or other mechanism to support fixed or removable storage media 514. For example, a hard disk drive, a solid-state drive, a magnetic tape drive, an optical drive, a compact disc (CD) or digital video disc (DVD) drive (R or RW), or other removable or fixed media drive might be provided. Storage media 514 might include, for example, a hard disk, an integrated circuit assembly, magnetic tape, cartridge, optical disk, a CD or DVD. Storage media 514 may be any other fixed or removable medium that is read by, written to or accessed by media drive 512. As these examples illustrate, the storage media 514 can include a computer usable storage medium having stored therein computer software or data.

In alternative embodiments, information storage mechanism 510 might include other similar instrumentalities for allowing computer programs or other instructions or data to be loaded into computing component 500. Such instrumentalities might include, for example, a fixed or removable storage unit 522 and an interface 520. Examples of such storage units 522 and interfaces 520 can include a program cartridge and cartridge interface, a removable memory (for example, a flash memory or other removable memory component) and memory slot. Other examples may include a PCMCIA slot and card, and other fixed or removable storage units 522 and interfaces 520 that allow software and data to be transferred from storage unit 522 to computing component 500.

Computing component 500 might also include a communications interface 524. Communications interface 524 might be used to allow software and data to be transferred between computing component 500 and external devices. Examples of communications interface 524 might include a modem or softmodem, a network interface (such as Ethernet, network interface card, IEEE 802.XX or other interface). Other examples include a communications port (such as for example, a USB port, IR port, RS232 port Bluetooth® interface, or other port), or other communications interface. Software/data transferred via communications interface 524 may be carried on signals, which can be electronic, electromagnetic (which includes optical) or other signals capable of being exchanged by a given communications interface 524. These signals might be provided to communications interface 524 via a channel 528. Channel 528 might carry signals and might be implemented using a wired or wireless communication medium. Some examples of a channel might include a phone line, a cellular link, an RF link, an optical link, a network interface, a local or wide area network, and other wired or wireless communications channels.

In this document, the terms "computer program medium" and "computer usable medium" are used to generally refer to transitory or non-transitory media. Such media may be, e.g., memory 508, storage unit 520, media 514, and channel 528. These and other various forms of computer program media or computer usable media may be involved in carrying one or more sequences of one or more instructions to a processing device for execution. Such instructions embodied on the medium, are generally referred to as "computer program code" or a "computer program product" (which may be grouped in the form of computer programs or other groupings). When executed, such instructions might enable the computing component 500 to perform features or functions of the present application as discussed herein.

It should be understood that the various features, aspects and functionality described in one or more of the individual embodiments are not limited in their applicability to the particular embodiment with which they are described. Instead, they can be applied, alone or in various combinations, to one or more other embodiments, whether or not such embodiments are described and whether or not such features are presented as being a part of a described embodiment. Thus, the breadth and scope of the present application should not be limited by any of the above-described exemplary embodiments.

Terms and phrases used in this document, and variations thereof, unless otherwise expressly stated, should be construed as open ended as opposed to limiting. As examples of the foregoing, the term "including" should be read as meaning "including, without limitation" or the like. The term "example" is used to provide exemplary instances of the item in discussion, not an exhaustive or limiting list thereof. The terms "a" or "an" should be read as meaning "at least one," "one or more" or the like; and adjectives such as "conventional," "traditional," "normal," "standard," "known." Terms of similar meaning should not be construed as limiting the item described to a given time period or to an item available as of a given time. Instead, they should be read to encompass conventional, traditional, normal, or standard technologies that may be available or known now or at any time in the future. Where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. The use of the term "component" does not imply that the aspects or functionality described or claimed as part of the component are all configured in a common package. Indeed, any or all of the various aspects of a component, whether control logic or other components, can be combined in a single package or separately maintained and can further be distributed in multiple groupings or packages or across multiple locations.

Additionally, the various embodiments set forth herein are described in terms of exemplary block diagrams, flow charts and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular architecture or configuration.

What is claimed is:

1. A dynamically formable electrodermal activity (EDA) sensor, comprising:
    a dynamically formable base comprising a formable surface configured to be dynamically formed in response to input signals;
    an EDA sensing layer affixed to the formable surface of the dynamically formable base, the EDA sensing layer comprising a plurality of sensors connected to a power supply; and
    a processor configured to determine an EDA of a user based on EDA measurements from the EDA sensing layer, wherein the input signals are based on the determined EDA of the user,
    wherein, in response to the input signals, the formable surface of the dynamically formable base and the EDA sensing layer affixed thereto are reformed into a desired contour.

2. The dynamically formable EDA sensor of claim 1, wherein the processor is further configured to provide the input signals to the dynamically formable base in response to pressure measurements to adjust the formable surface of the dynamically formable base to conform to a body part of the user.

3. The dynamically formable EDA sensor of claim 1, wherein the dynamically formable base comprises a plurality of separately actuatable elements arranged in a matrix, such that controlling the input signals to each of the separately actuatable elements determines a result in contour of the formable surface.

4. The dynamically formable EDA sensor of claim 1, wherein the dynamically formable base comprises a soft robotics material.

5. The dynamically formable EDA sensor of claim 1, wherein the EDA sensing layer comprises a plurality of electrodes on a flexible substrate, and wherein the processor is configured to evaluate a connection strength between electrodes of the EDA sensing layer and skin of the user at a given time and to identify electrodes from which EDA measurements are to be made based on the evaluation.

6. The dynamically formable EDA sensor of claim 5, wherein the processor is further configured to determine the EDA of the user based on EDA measurements from the identified electrodes.

7. The dynamically formable EDA sensor of claim 5, wherein the EDA of the user is determined based on a combination of measurements from the identified electrodes.

8. The dynamically formable EDA sensor of claim 1, wherein the dynamically formable base is configured to be reformed to conform to at least a portion of a hand of the user.

9. The dynamically formable EDA sensor of claim 1, wherein the dynamically formable base is configured to be reformed to provide a haptic response to the user of the dynamically formable EDA sensor.

10. The dynamically formable EDA sensor of claim 1, wherein the dynamically formable base is configured to be reformed to provide one or more raised regions on the formable surface based on the input signals, each of the one or more raised regions indicating a button configured to receive a user input.

11. A hybrid electrodermal activity (EDA) sensor and user input device, comprising:
a flexible EDA layer comprising a first flexible substrate and a plurality of electrodes disposed on the first flexible substrate;
a flexible actuation layer affixed to the flexible EDA layer, the flexible actuation layer comprising electrical contacts disposed on a second flexible substrate; and
a processor configured to determine an EDA of a user based on EDA measurements from one or more electrodes of the plurality of electrodes and provide an input signal to a formable surface based, in part, on the determined EDA of the user, wherein the formable surface is formed into a desired contour in response to the input signal.

12. The hybrid EDA sensor and user input device of claim 11, wherein the first and second flexible substrates comprise transparent substrates, and wherein the plurality of electrodes disposed on the first flexible substrate and the electrical contacts disposed on the second flexible substrate comprise transparent conductive materials.

13. The hybrid EDA sensor and user input device of claim 11, wherein the processor is further configured to provide the input signal to the flexible actuation layer based on an amount of pressure applied by the user to the flexible EDA layer.

14. The hybrid EDA sensor and user input device of claim 11, wherein the processor is further configured to evaluate a connection strength between electrodes of the flexible EDA layer and skin of the user at a given time and to identify electrodes from which the EDA measurements are to be made based on the evaluation.

15. The hybrid EDA sensor and user input device of claim 14, wherein the processor is further configured to determine the EDA of the user based on the EDA measurements from the identified electrodes.

16. The hybrid EDA sensor and user input device of claim 14, wherein the EDA of the user is determined based on a combination of measurements from the identified electrodes.

17. A system for processing information from a plurality of electrodermal activity (EDA) sensors to determine an EDA of a user, comprising:
a processor; and
a non-transitory memory coupled to the processor and configured to store instructions, the instructions, which when executed cause the processor to perform operations comprising:
receiving information from a plurality of electrodes of an EDA sensor;
determining an EDA measurement for the user based on the information received from the plurality of electrodes; and
providing an input signal to a formable surface based, in part, on the determined EDA measurement for the user, wherein the formable surface is formed into a desired contour in response to the input signal.

18. The system of claim 17, wherein determining an EDA measurement comprises computing a weighted average of EDA measurements from the plurality of electrodes.

19. A method of processing information from a plurality of electrodermal activity (EDA) sensors to determine an EDA of a user, comprising:
receiving information from a plurality of electrodes of an EDA sensor;
determining an EDA measurement for the user based on the information received from the plurality of electrodes; and
providing an input signal to a formable surface based, in part, on the determined EDA measurement for the user, wherein the formable surface is formed into a desired contour in response to the input signal.

20. The method of claim 19, wherein determining an EDA measurement comprises computing a weighted average of EDA measurements from the plurality of electrodes.

* * * * *